United States Patent [19]

Yoshida et al.

[11] Patent Number: 4,913,138
[45] Date of Patent: Apr. 3, 1990

[54] ADHESIVE BANDAGE FOR PERSONAL USE

[76] Inventors: Haruo Yoshida, 5-1406, Onoe-danchi 1-2, Onoe-cho, Nagoya-shi, Aichi-ken; Shoichi Kume, 150-2, Ninowari, Kabuoto-cho, Tsushima-shi, Aichi-ken, both of Japan

[21] Appl. No.: 265,556

[22] Filed: Nov. 1, 1988

[30] Foreign Application Priority Data

Nov. 7, 1987 [JP] Japan .......................... 62-170552[U]

[51] Int. Cl.$^4$ .............................................. A61L 15/00
[52] U.S. Cl. .................................... 128/155; 128/156; 128/157; 206/441
[58] Field of Search ............... 128/155, 157, 165, 169, 128/885, 893, D25, 156; 206/441

[56] References Cited

U.S. PATENT DOCUMENTS

| 2,880,863 | 4/1959 | Stanton | 206/441 |
|---|---|---|---|
| 4,265,234 | 5/1981 | Schaar | 204/441 X |
| 4,696,393 | 9/1987 | Laipply | 206/441 X |
| 4,781,293 | 11/1988 | Johns | 128/156 X |
| 4,826,009 | 5/1989 | Young | 206/441 X |
| 4,832,008 | 5/1989 | Gilman | 128/156 X |
| 4,832,009 | 5/1989 | Dillon | 128/156 |

FOREIGN PATENT DOCUMENTS

| 52-140804 | 5/1979 | Japan . |
|---|---|---|
| 52-161258 | 6/1979 | Japan . |
| 52-161881 | 6/1979 | Japan . |
| 52-167703 | 7/1979 | Japan . |
| 57-99948 | 3/1983 | Japan . |
| 56-186996 | 6/1983 | Japan . |
| 59-15980 | 8/1984 | Japan . |
| 59-57501 | 10/1984 | Japan . |
| 60-38279 | 9/1986 | Japan . |
| 62-189660 | 5/1988 | Japan . |

Primary Examiner—Richard J. Apley
Assistant Examiner—N. Paul
Attorney, Agent, or Firm—Fred Philpitt

[57] ABSTRACT

An adhesive bandage used personally to cover a minor injury on a human body, especially on a finger or a toe thereof, comprises a bandage proper having an adhesive inside, a pad fixed to a substantially central portion of the inside of the bandage proper, and a protective paper having opposed end portions removably attached to the inside of the bandage proper. The protective paper has a central, greater part folded flatwise. The central greater part of the protective paper can be unfolded and has a sufficient length to provide, together with the bandage proper, an ample space through which a finger or a toe with a minor injury to be covered can be inserted, when the central greater part is unfolded. Another adhesive bandage for personal use comprises a bandage proper having an adhesive side, a pad fixed to a substantially central portion of the adhesive side of the bandage proper for directly covering a minor injury, a loop means having opposed end portions removably attached to opposed end portions of the adhesive side of the bandage proper, and a protective paper having a substantially central, greater part removably attached to the adhesive side of the bandage proper. The loop means has a sufficient length to form, together with the bandage proper, a loop which defines an expandable space through which fingers can be inserted.

7 Claims, 5 Drawing Sheets

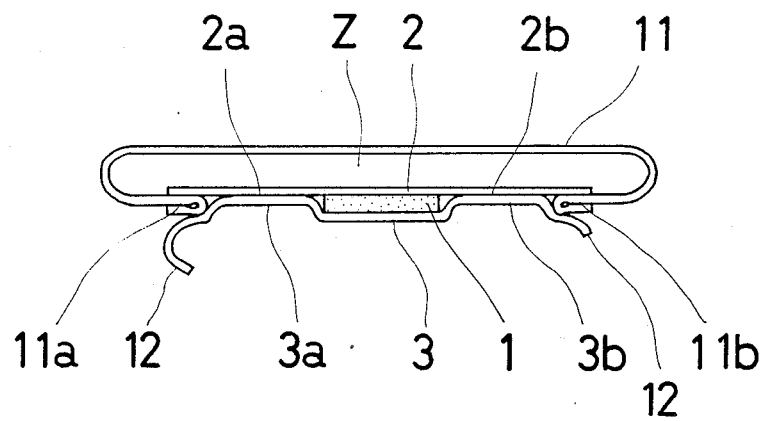
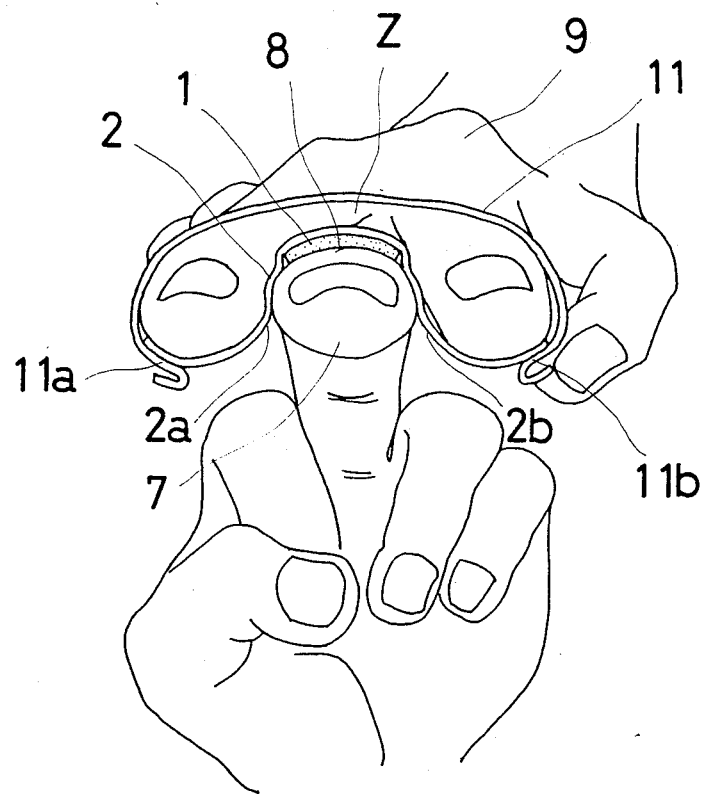

ADHESIVE BANDAGE FOR PERSONAL USE

FIELD OF THE INVENTION

This invention relates to an adhesive bandage used personally to cover a minor wound, such as a small abrasion or a small cut, or a minor burn on a human body, more particularly on a finger or a toe.

BACKGROUND OF THE INVENTION

A typical example of a conventional adhesive bandage used personally to cover a minor wound or a minor burn on a human body is illustrated in FIG. 25 of the drawing of Japanese Pat. Application No. 60-38279 published in Japanese Official Gazette of Pat. Application No. 61-196958. The adhesive bandage illustrated therein comprises (i) a strip of tape, or bandage proper, having an adhesive inside and (ii) a gauze pad fixed to the center of the inside and covered with two sheets of protective paper. In use, the protective papers are removed to expose the pad, and the bandage proper is applied on a minor wound or burn so as to cover the injury exactly with the pad.

There is a case where, although a wound or burn is one of a minor nature on a finger of one hand, only the other hand can be used to cover the injury. Thus, in such a case, in order to cover the injury with the foregoing conventional bandage, its protective papers must be removed and the bandage proper must be applied to the injury so as to cover it exactly with the pad, only b one hand. However, such operations are not always easy. Also, in such a case, if the conventional bandage is used, the bandage proper may be accidentally applied on a position other than the intended position before the user is able to apply it on the intended position. Moreover, in such a case, with the conventional bandage, different portions of the inside, or adhesive side, of the bandage proper may stick to each other before the user can apply it on the intended position. Also, there is a case where, although one of two sides of the inside of the bandage proper opposed to each other with was correctly applied, different portions of the other side may stick to each other. Thus, with the conventional bandage, if only one hand can be used to cover the injury, it is possible that the user may not succeed in applying the bandage proper only at one time, but may let it or some portion of it stick to an unintended portion before being able to apply it correctly. And, in such an event, the user makes one more attempt to correctly apply the bandage proper, but the portion of it which stuck to the unintended portion in the previous attempt no longer has the same adhesive strength as before and, hence, it may be necessary for the user to throw away the useless bandage and use a new bandage.

SUMMARY OF THE INVENTION

It is an object of the invention to provide an adhesive bandage used personally to cover a minor injury on a human body, more particularly on a finger or a toe.

Another object of the invention is to provide an adhesive bandage for personal use which is particularly adapted for application on an injury on a finger which is a minor one, but which is of such a nature that only the hand not injured can be used to cover it.

Other objects and advantages of the invention will become apparent upon reading a detailed description of the preferred embodiments which will follow.

According to one aspect of the invention, an adhesive bandage used personally to cover a minor injury includes a bandage proper having an adhesive inside, a pad fixed to a substantially central portion of the inside of the bandage proper for directly covering a minor injury, and a means for protecting both the pad and the inside of the bandage proper which is removably attached, at its opposed end portions, to two sides of the inside of the bandage proper opposed to each other with the pad between. The protecting means has a central greater part not attached to any portion of the bandage proper nor to the pad, but folded flatwise so as to make the entire bandage a relatively flat bandage. The central greater part of the protecting means can be unfolded and has a sufficient length to provide, together with the bandage proper, an ample space through which a finger or a toe with a minor injury to be covered can be inserted, when the central greater part of the protecting means is in the state of being unfolded. The bandage proper is applied on the injury to cover the injury exactly with the pad. After the insertion of a finger or toe injured through the foregoing space and the covering of its injury with the pad, the protecting means is pulled in different directions in a successive manner, thereby attaching the opposed two sides of the inside of the bandage proper to the finger or toe while simultaneously removing the opposed end portions of the protecting means from the opposed two sides of the inside of the bandage proper.

For a minor injury on a portion of a body other than a finger or a toe, the protecting means can be turned by substantially 180 degrees without removing the extreme end portions of the protecting means from the opposed two sides of the inside of the bandage proper, so that an outside surface of the protecting means immediately after when the protecting means has been unfolded forms an inside surface and so that this inside surface, together with a surface of the bandage proper opposed to the inside surface of the bandage proper, forms an ample space through which two fingers, for example, can be inserted.

According to another aspect of the invention, an adhesive bandage used personally to cover a minor injury includes a bandage proper having an adhesive side, a pad fixed to a substantially central portion of the adhesive side of the bandage proper for directly covering a minor injury, a loop means removably attached, at its opposed end portions, to opposed end portions of the adhesive side of the bandage proper, and means for protecting both the pad and the adhesive side of the bandage proper. The protecting means has a substantially central, greater part removably attached to the adhesive side of the bandage proper to protect both the pad and the adhesive side of the bandage proper. The loop means has a sufficient length to form, together with the bandage proper, a loop which defines an expandable space through which fingers can be inserted. The foregoing loop is located on the side opposed to the side of the pad with the bandage proper between. Thus, after the protecting means has been removed from the bandage proper, the bandage proper can be applied on the injury to cover the injury exactly with the pad while supporting, with fingers inserted through the foregoing space, the surface of the bandage proper opposed to the adhesive surface thereof.

BRIEF DESCRIPTION OF THE DRAWING

FIG. 10 shows an adhesive bandage which embodies the invention in another preferred form; and FIG. 11 illustrates an example of how to use the bandage of FIG. 10.

DETAILED DESCRIPTION OF THE PREFERRED EMBODIMENTS

First Preferred Embodiment

Figure 1:
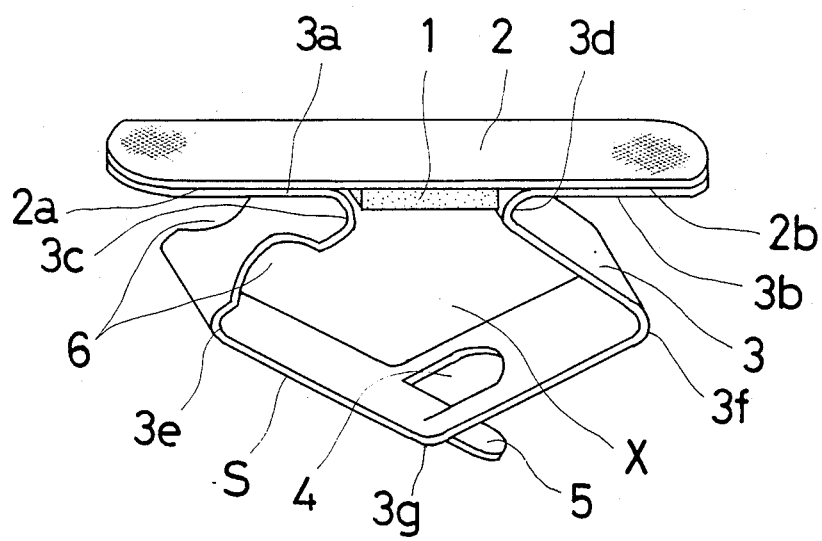
FIG. 1 is a perspective view of an adhesive bandage which embodies the invention in one preferred form.
Figure 7:
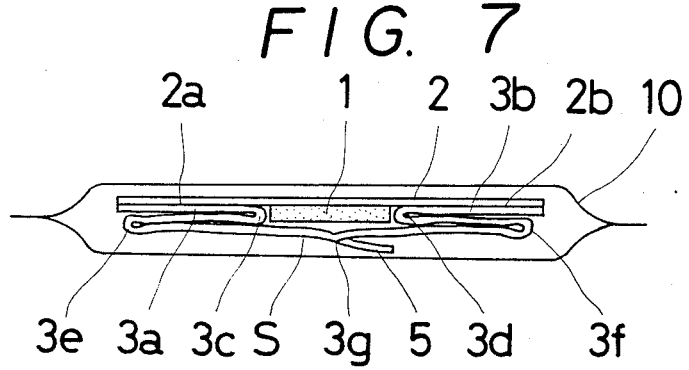
FIG. 7 illustrates the bandage of FIG. 1 with a central, greater part of its protective paper folded flatwise to make the entire bandage a relatively flat product for convenience of the sale to customers of the bandage as a compact product.
Figure 8:
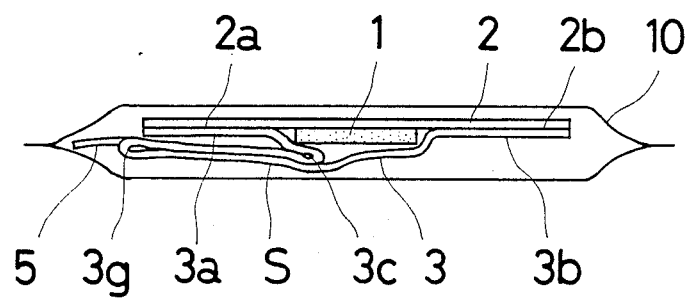
FIG. 8 illustrates the bandage of FIG. 1 with the central, greater part of its protective paper folded flatwise in a manner different from that of FIG. 7, but for the same purpose as in FIG. 7.

Referring now to the drawing, FIG. 1 depicts an adhesive bandage for personal use which embodies the invention in one preferred form. The bandage of FIG. 1 includes (i) a strip of tape, or bandage proper, 2 having an adhesive inside (, or an adhesive lower side) and (ii) a pad 1 fixed to the inside of the tape 2. A single sheet of protective paper 3 is attached, at opposed end portions 3a and 3b thereof, to two sides 2a and 2b of the inside of the tape 2 opposed to each other with the pad 1 between, respectively. In use, the bandage is applied to a minor injury on a portion of a human body such as a finger in such a manner that the pad 1 covers the injury exactly. The pad 1 may be made of cotton gauze or any other suitable material. Also, the pad 1 is usually located at the center of the inside of the tape 2. In FIG. 1, as illustrated, the central portion S of the protective paper 3, or its portion other than its opposed end portions 3a and 3b, is hanging down from the end portions 3a and 3b. However, before the bandage is used, or when the bandage is sold to a customer, the central portion S of the protective paper 3 is in the state of being folded flatwise, e.g., as illustrated in FIGS. 7 or 8, to make the entire bandage a relatively flat product for convenience of the sale to customers of the bandage as a compact product. In use, the central portion S is unfolded as illustrated in FIG. 1. The central portion S of the paper 3 has a greater length than the tape 2.

Usually the central portion S of the protective tape 3 is folded as illustrated in FIG. 7. In FIG. 7, the central portion S is folded outwardly at its opposed upper portions 3c and 3d, and then is folded inwardly at its middle opposed portions 3e and 3f, and finally is folded to the right side at its lower portion 3g. As illustrated, when the central portion S is in the state of being folded in such a manner, the central portion S has substantially the same length as the tape 2 as viewed from above or below.

As mentioned above, in use, the central portion S of the protective paper 3 is unfolded as illustrated in FIG. 1. As illustrated in FIG. 1, when the central portion S is thus unfolded, it provides a generally diamond-shaped space X which is more than sufficient for the user to insert his finger 7 with an injury 8 therethrough without causing the injury 8 to touch the pad 1. It will be appreciated that a toe (not shown) also can be inserted through the space X.

If the bandage is designed exclusively for a minor injury only on a finger or a toe, the protective paper 3 is formed with from about one and half times to about three times the length of the bandage proper 2. However, if the bandage is designed to cover a minor injury either on a finger or a toe or on a wrist or an ankle, the protective paper 3 is formed with a greater length.

The central portion S of the protective paper 3 is cut a little to the right of the center thereof to provide both an opening 4 and a tab 5. The user of the bandage may hold the tab 5 to readily unfold the central portion S. However, although, in FIG. 7, the tab 5 is outside the opening 4, there may a case that the tab is wholly or substantially inside the opening. In such a case it may be difficult for the user to put out the tab 5 from the opening 4 in order to provide a portion to be held to readily unfold the central portion. However, a pair of opposed cuts 6 are provided between one 3c of the upper opposed portions of the central portion S and one 3e of the middle opposed portions thereof. And If it is difficult for the user to put out the tab 5 from the opening 4, the user may hold the portions of the central portion S which are located directly below the cuts 6 when the central portion is in the folded state of FIG. 7. If the user holds such portions, the user can unfold the central portion not only readily, but without touching the pad 1, as is the case where the user holds the tab 5.

First Example of How to Use the Bandage of the First Preferred Embodiment

Figure 2:
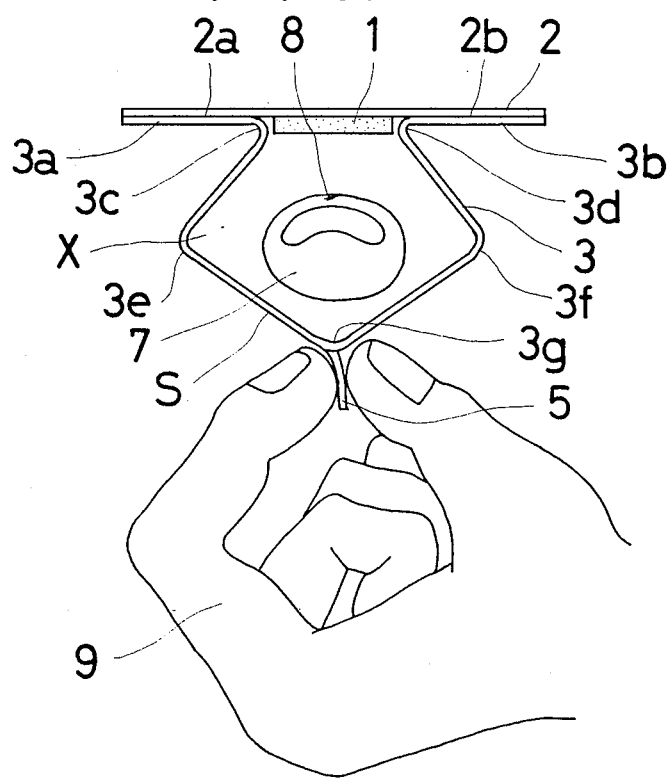
FIGS. 2 to 6 illustrate an example of how to use the bandage of FIG. 1.
Figure 3:
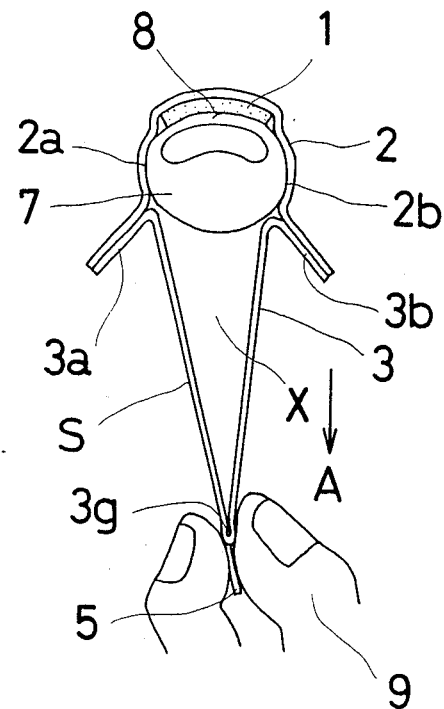
Figure 4:
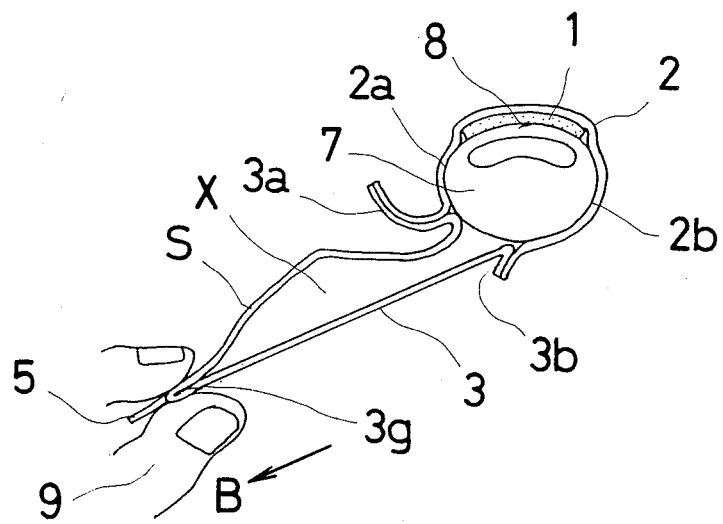
Figure 5:
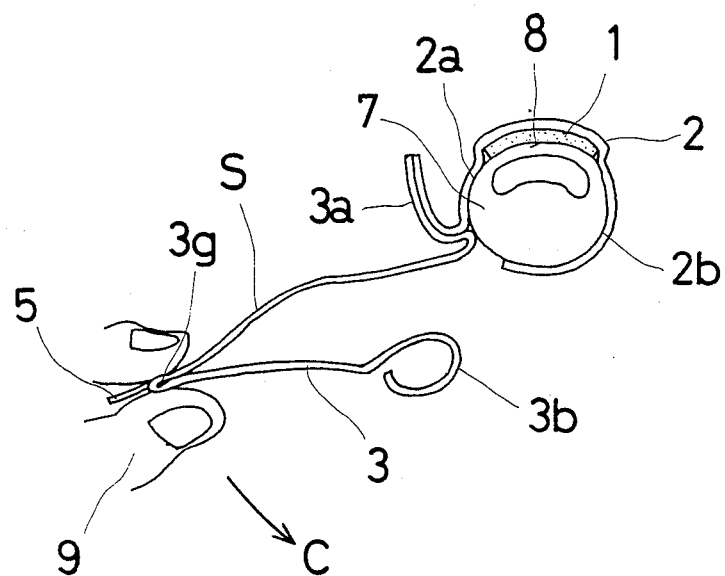

Description will now be made of an example of how to use or apply the above-mentioned bandage on a minor injury on a finger. Usually the bandage is sold in the state of being packaged as illustrated in FIG. 7. First the bandage is taken out from a package 10. Then, the tab 5 is held with the hand not injured. As mentioned above, however, if the tab 5 is wholly or substantially inside the opening 4 and cannot be put out easily from the opening 4, the portions of the central portion S directly below the cuts 6 may be held. Or any other portion of the central portion S may be held which allows the user to unfold the central portion S without touching the pad 1. Then, the central portion S of the protective paper 3 is unfolded to provide a space X. Thereafter, the finger 7 injured at 8 is inserted through the space X (FIG. 2). Then, the pad 1 is applied exactly to the injury 8 (FIG. 3), and the lower portion 3g of the central portion S is held with the hand 9 not injured (FIG. 3). Then, the protective paper 3 is pulled down, or in a direction A of FIG. 3, so as to detach about the inner half of each of the opposed end portions 3a and 3b of the paper 3 from the adhesive tape, or the bandage proper, 2 and attach about the inner halves of the opposed sides 2a and 2b of the inside of the tape 2 (, or the adhesive side thereof) to two sides of the finger 7 opposed to each other with the injury 8 between, respectively (FIG. 3). Then, the paper 3 is pulled in a direction B of FIG. 4 to detach the remaining portion of the right-hand end portion 3b of the paper 3 from the tape 2 and attach the remaining portion of the right-hand side 2b of the inside of the tape 2 to the finger (FIG. 5). Then, the paper 3 is turned to a direction C of FIG. 5, and is pulled in a direction D of FIG. 6 to detach the remaining portion of the left-hand end portion 3a of the paper 3 from the tape 2 and attach the remaining portion of the left-hand side 2a of the inside of the tape on the right-hand end portion of the tape. Thus, the protective paper 3 is completely detached from the adhesive tape 2, and the finger 7 with its injury 8 is completely bandaged at its required portion.

Figure 6:
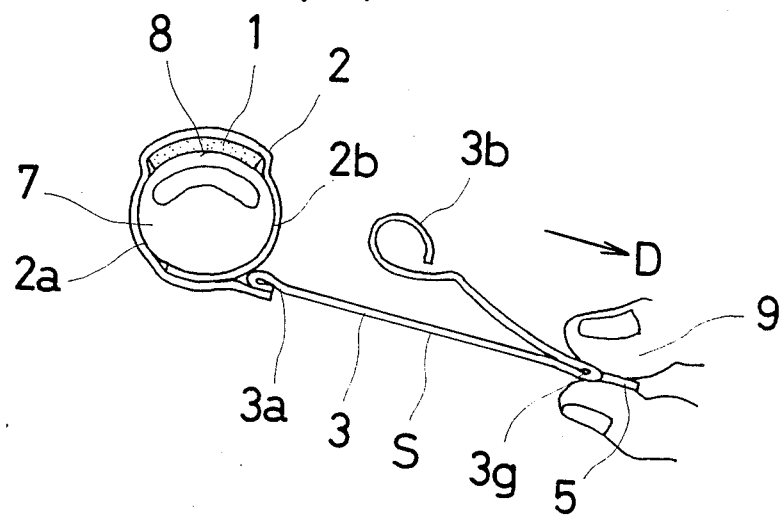

Needless to say, if desired, subsequently to the pulling of the protective paper 3 in the direction A of FIG. 3 the paper 3 may be pulled in the direction D of FIG. 6 and then in the direction B of FIG. 4.

It will be appreciated that the use of the bandage of the invention enables the injury to be bound up exactly and very readily even if only the hand not injured can be used for the binding operation.

Second Example of How to Use the Bandage of the First Preferred Embodiment

Figure 9:
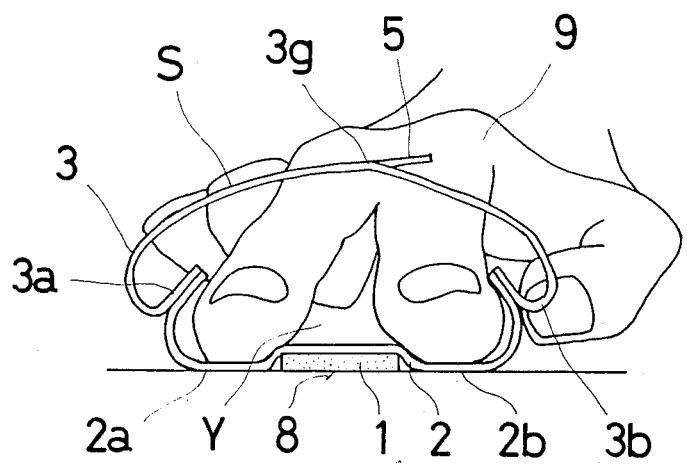
FIG. 9 illustrates another example of how to use the bandage of FIG. 1.

Referring to FIG. 9, description will now be made of an example of how to apply the bandage of the first embodiment on a minor injury on a portion of a body other than a finger or a toe. For such an injury, the protective paper 3 may be turned upward by substantially 180 degrees from its position of FIG. 1 and without detaching the extreme end portions of the paper 3 from the tape 2, so that the outside surface of the paper 3 when the paper 3 is in the position of FIG. 1 forms an inside surface, as illustrated in FIG. 9. As illustrated, this inside surface is part of the whole inside surface which defines a space Y produced by turning the paper 3 in the above-mentioned manner. Then, two fingers, for instance, are inserted through the space Y to touch and support the side portions of the tape 2 opposed to each other with the pad 1 between. Then, the pad 1 is applied exactly to the injury. In FIG. 9 the injury is designated by numeral 8. Then, the portions of the adhesive side of the tape 2 which have already been exposed are attached to areas of the skin opposed to each other with the injury between. Then, the fingers are moved away from both the tape 2 and the space Y, and while detaching the remaining portions of the paper 3 from the tape 2, the remaining portions of the adhesive side of the tape are attached to the skin. Or, subsequently to the attachment of the foregoing exposed portions of the adhesive side of the tape 2 to the foregoing areas of the skin, the paper 3 may be pulled in the direction opposite to the injury (, or in an upward direction if the bandage is applied on the injury from above as in FIG. 9) with one hand while supporting the tape 2 and attaching the remaining portions of its adhesive side to the skin with the fingers of the other hand.

Modifications

As mentioned before, when the bandage is sold to a customer, usually the central portion S of the protective paper 3 is in the state of being folded as illustrated in FIG. 7, i.e., in a generally symmetrical manner. However, the central portion S may be folded in any other suitable manner, including the manner as illustrated in FIG. 8.

In the foregoing embodiment the single sheet of protective paper 3 is used. However, according to the spirit of the invention, the two sheets of protective paper used for the conventional adhesive bandage may be connected by a suitable connecting means (such as a sheet of paper, thread or a string) having a sufficient length to form, together with the bandage proper, an ample space for receiving a finger injured, so as to provide an adhesive bandage having essentially the same principal merit as the bandage of the invention, namely, the merit of enabling a minor injury on a finger of one hand to be bound up readily only with the other hand. Also, according to the spirit of the invention, the conventional adhesive bandage may be modified by providing the bandage proper with two sheets of protective paper having a total length substantially equal to the length of the single protective paper 3 and connected to each other by a suitable means, so as to provide an adhesive bandage of the invention having essentially the same principal merit as the bandage of the invention.

If required, the protective paper 3 may be cut into two at its lower portion 3g or thereabout to use the bandage in the same manner as the conventional adhesive bandage.

Second Preferred Embodiment

FIG. 10 depicts an adhesive bandage for personal use which embodies the invention in another preferred form. The bandage of FIG. 10 comprises (i) a strip of tape, or bandage proper, 2 having an adhesive lower side, (ii) a pad 1 fixed to the adhesive side of the tape 2, (iii) a loop means 11 attached, at its opposed end portions, to the opposed end portions of the adhesive side of the tape 2 to form, together with the tape 2, a loop which defines an expandable space Z for receiving fingers, and (iv) a single sheet of protective paper 3 with a substantially central, greater part attached to the adhesive side of the tape 2 to cover the pad 1 and with opposed tab portions 12.

Example of How to Use the Bandage of the Second Preferred Embodiment

Referring to FIG. 11, an example of how to use the bandage of the second preferred embodiment will now be described. First, two fingers of one hand 9, for example, are inserted through the space Z as illustrated in FIG. 11. As illustrated, when the fingers are inserted through the space Z, the space Z is expanded. Then, one of the tab portions 12 is held, and the protective paper 3 is detached from the tape 2 to expose the pad 1. Then, the bandage is applied on a minor injury 8, e.g., on a finger 7 of the other hand so as to cover the injury 8 exactly with the pad 1. Then, the inner portions of two sides 2a and 2b of the adhesive side of the tape 2 opposed to each other with the pad 1 between are attached to the finger 7 with the fingers of the other hand 9 inserted through the space Z. Then, the fingers of the hand 9 are taken out from the space Z, and the loop means 11 is removed from the tape 2 while lightly pressing the portion of the tape 2 to which the pad 1 is fixed, so as not to allow the bandage to remove from the finger 7. Then, the remaining portions of the opposed sides 2a and 2b of the adhesive side of the tape 2 are attached to the finger 7 in such a manner that the opposed end portions of the tape 2 overlap each other.

It will be appreciated that the use of the bandage of either the first preferred embodiment or the second preferred embodiment enables a minor injury on a finger to be bound up exactly and very readily even if only the hand not injured or the less skillful hand can be used for the binding operation.

What is claimed is:

1. An adhesive bandage used personally to cover a minor injury on a human body, especially on a finger or a toe thereof, which is particularly suitable for application with only one hand and which comprises (i) a backing strip having an adhesive inside, (ii) a pad fixed to a substantially central portion of the inside of the backing strip for directly covering a minor injury, (iii) a protecting means for protecting both the pad and the inside of the backing strip, said protecting means being removably attached, at its opposed end portions, to two sides of the inside of the backing strip opposed to each other with the pad between, (iv) said protecting means having a central, greater part not attached to any portion of the backing strip not to the pad, but folded flatwise so as to make the entire bandage a relatively flat product for convenience of sale of the bandage to customers as a compact product, (v) said central greater part of said protecting means being capable of being unfolded and a having a sufficient length to provide, together with the backing strip, a substantially completely enclosed, ample space through which a finger or a toe with a minor injury to be covered can be inserted when said central greater part is in the state of being unfolded, and (vi) the backing strip being capable of being applied on the injury to cover the injury exactly with the pad, and said protecting means being capable of being pulled in different directions in a successive manner after the insertion of an injured finger or toe through said space and the covering of its injury with the pad, thereby attaching said opposed two sides of the inside of the backing strip to an area of the finger or toe other than its area of the injury while simultaneously removing said opposed end portions of said protecting means from said opposed two sides of the inside of the backing strip.

2. An adhesive bandage in accordance with claim 1 wherein, after being unfolded, said protecting means can be turned by substantially 180 degrees without removing the extreme end portions of said protecting means from said opposed two sides of the inside of the backing strip, so that an outside surface of said protecting means immediately after said protecting means has been unfolded forms an inside surface, and so that said inside surface together with a surface of the backing strip opposed to the inside surface of the backing strip, forms a substantially completely enclosed, angle space through which more than one finger can be inserted to apply the bandage on a minor injury on a portion of a body other than a finger or a toe.

3. An adhesive bandage in accordance with claim 1 wherein said protecting means has a tab means which can be held to pull said protecting means in said different directions.

4. An adhesive bandage in accordance with claim 2 wherein said protecting means has a tab means which can be held to pull said protecting means in said different directions.

5. An adhesive bandage in accordance with any one of claims 1 to 4 wherein said protecting means comprises a single continuous tape.

6. An adhesive bandage in accordance with any one of claims 1 to 4 wherein said protecting means comprises two separate tapes connected directly to each other.

7. An adhesive bandage in accordance with any one of claims 1 to 4 wherein said protecting means comprises two separate tapes with substantially equal and relatively great lengths and a separate middle tape with a smaller length than said two separate tapes which connects said two separate tapes.

* * * * *